United States Patent
Lynch

(10) Patent No.: US 10,342,481 B2
(45) Date of Patent: Jul. 9, 2019

(54) DEVICES, SYSTEMS AND METHODS FOR UNOBTRUSIVELY MONITORING PATIENT VITAL SIGNS

(71) Applicant: Meghan Maureen Lynch, Denver, CO (US)

(72) Inventor: Meghan Maureen Lynch, Denver, CO (US)

(73) Assignee: Meghan Lynch

( * ) Notice: Subject to any disclaimer, the term of this patent is extended or adjusted under 35 U.S.C. 154(b) by 355 days.

(21) Appl. No.: 15/256,690

(22) Filed: Sep. 5, 2016

(65) Prior Publication Data

US 2018/0064393 A1    Mar. 8, 2018

(51) Int. Cl.
| | |
|---|---|
| *A61B 5/00* | (2006.01) |
| *A42B 1/24* | (2006.01) |
| *A61B 5/0205* | (2006.01) |
| *A61B 5/1455* | (2006.01) |
| *A61B 5/01* | (2006.01) |
| *A42B 1/04* | (2006.01) |

(52) U.S. Cl.
CPC .......... *A61B 5/6803* (2013.01); *A42B 1/041* (2013.01); *A42B 1/242* (2013.01); *A61B 5/0002* (2013.01); *A61B 5/01* (2013.01); *A61B 5/02055* (2013.01); *A61B 5/14552* (2013.01)

(58) Field of Classification Search
CPC ....... A42B 1/041; A42B 1/242; A61B 5/0002; A61B 5/01; A61B 5/02055; A61B 5/14552; A61B 5/6803
USPC .................................. 600/300, 301
See application file for complete search history.

(56) References Cited

U.S. PATENT DOCUMENTS

| | | | | |
|---|---|---|---|---|
| 2013/0104288 A1* | 5/2013 | Schlottau | ............... | A41D 1/002 2/209.13 |
| 2013/0110415 A1* | 5/2013 | Davis | ..................... | A42B 3/046 702/41 |
| 2018/0295919 A1* | 10/2018 | Shearman | .............. | A42B 3/042 |

OTHER PUBLICATIONS

Covidien, Nellcor SpO2 Forehead Sensor—product brochure, 2010, captured on-line on Aug. 31, 2016 at: http://www.medtronic.com/content/dam/covidien/library/us/en/legacyimport/patientmonitoringrecovery/patientmonitoring/7/nellcor-maxfast-spo2-forehead-sensorbrochure.pdf.
Philips, Philips Intellivue MMS X2 Multi-measurement Module, Jul. 1, 2015, 2 pages, captured on-line on Aug. 31, 2016 at: http://incenter.medical.philips.com/doclib/enc/12201389/IntelliVue_MMS_X2_brochure_452299109431.pdf%3ffunc%3ddoc.Fetch%26nodeid%3d12201389.

* cited by examiner

*Primary Examiner* — Michael J Carey
(74) *Attorney, Agent, or Firm* — Wash Park IP Ltd.

(57) ABSTRACT

Various embodiments of devices, systems and methods for using a cap to unobtrusively monitor a patient's vital signs are disclosed. More specifically, a stocking cap includes at least one primary compartment configured for receiving a first biometric sensor, at least one third compartment configured for receiving a cartridge, at least one fourth compartment configured for receiving a transmitter, at least one channel configured for routing at least one connector, and at least one fifth compartment configured for receiving an antenna. A system for use with such a cap includes a sensor which outputs vitals, a cartridge configured to receive the vitals from the sensor, process the received vitals, and output the processed vitals to a server. The server providing processed vital signals for use and display on a tablet or other user presentation and user interface device.

19 Claims, 4 Drawing Sheets

DEVICES, SYSTEMS AND METHODS FOR UNOBTRUSIVELY MONITORING PATIENT VITAL SIGNS

FIELD

The technology described herein relates to devices, systems and methods for unobtrusively monitoring patient vital signs. The described technologies also relate to devices, systems and methods for remotely monitoring patient vital signs. The technology described herein also relates to devices, systems and methods for continuously monitoring patient vital signs.

BACKGROUND

In a hospital and like environments, patients are often connected to one or more vital and other biological indicator ("vital sign" and "vitals") monitoring devices. Such devices measure, for example, patient vital signs including heart rate, temperature, peripheral capillary oxygen saturation ("SpO2"), blood pressure and others. Other patient vital signs may also be monitored. Often, to obtain an accurate measurement of one or more of such vital signs, a nurse or other medical practitioner (for purposes herein, collectively, a "nurse") will often personally administer a vital sign monitoring device to the patient. For example, a nurse might use a hand-held sensor to take the patient's temperature. It is to be appreciated, however, that such an approach often requires awakening the patient or otherwise disturbing the patient's state of being. For some patients, such as young children, the mentally ill, violent prisoners and older patients, the providing of such direct patient monitoring may disrupt a patient's sleep cycle, delay healing, cause undue patient stress, put the nurse at risk, or result in an unexpected or undesired reaction. For example, the patient's temperature, heart rate or other vitals may rise or otherwise change due to the nurse's presence. The raising of such other vital signs may impact the accuracy and/or trending of the vital then being monitored. Further, such direct monitoring often requires the physical presence of the nurse next to the patient. In many settings, such presence may be interrupted or precluded by other events or conditions (such as may arise in an isolation ward) and/or the needs of other patients. Often this need for direct monitoring and the preclusion thereof, results in unreliable and aperiodic sampling. Accordingly, the monitoring of a patient's given vital sign(s) often will not and cannot occur continuously or even on a predetermined or given schedule. As such, direct, in-person monitoring of patient vital signs is often undesirable or impractical.

Another approach for monitoring patient vital signs has recently arisen. Per this approach, a sensor is physically connected to the patient, with the sensor being connected by a wire to a monitoring device, which may have a local and/or remote readout capability (for example, at a nursing station). For example, an SpO2 sensor is often connected to a patient's index finger via a clamp type device connected to an electrical wire, which in turn is connected to a local monitoring and alarm device. As any patient that has been connected to such a device can attest, such approach of indirectly monitoring a patient's vital sign (in this example SpO2) is undesirable for a wide variety of psychological and physical reasons.

First, the ever present clamp and cabling is very obtrusive, especially when the patient is connected to intra-venous (IV) lines and other treatment and/or monitoring devices. The presence of this ever present and obtrusive monitoring device reinforces to a patient that they are ill and often manifests as inducing additional patient stress. Likewise, the associated cabling connecting a sensor on a patient to a monitoring device, or other fixed or mobility challenging equipment often renders an otherwise simple task, such as leaving one's bed to attend to one's personal needs, an ordeal requiring nursing assistance. Given the time constraints on such nursing assistance, these hard-wired approaches can in turn induce undue stress and/or discomfort in the patient.

Second, the ever present SpO2 clamp, for example, is often uncomfortable as it and similar monitoring devices require a certain amount of pressure on one's finger that is ever present and thus disturbs the patient's desired state of tranquility, whether it be sleep, resting, while changing of television channels, or otherwise.

Third, these types of sensors are routinely falling off or otherwise sending false and inaccurate signals. Certain patient populations may also be prohibited from using finger and similar sensors due to peripheral neuropathy, poor peripheral perfusion or other conditions. While some providers have introduced forehead based vital monitoring devices and while such an approach is commonly more acceptable to a majority of patient populations, currents approaches are obtrusive. A patient knowingly connected, via sensors on their head, to diagnostic devices induces patient stress. Further, current approaches often result in undesirable audible alarms generated by locally present diagnostic devices. Such alarms further induce patient stress, for example, by disturbing the patient's rest. Such false alarms also often impinge on a nurse's already often full shift schedules.

Fourth, due to the nature of the types of sensors used, such sensors typically support monitoring of only a single vital. Accordingly, a patient often ends up connected to multiple devices and multiple sensors, each monitoring a single vital sign, and each being often very obtrusive upon the patient's comfort and mental and physical well-being. These combinations of elements, i.e., the need for monitoring of multiple vital signs, obtrusive sensors, and/or the need for frequent nurse presence result in undue patient physical and mental stress. Such stresses and their associated disruptions, often preclude reliable and continues monitoring of a patient's vital signs.

Notably, various recent designs of SpO2 and similar sensors have been developed that seek to address some of the above concerns. none provide the easy to use and non-obtrusive characteristics of the various embodiments of the present disclosure, as provided below. Notably, various of these newer designs attempt to address the issues of finger based sensors by affixing a sensor on a patient's forehead using an adhesive and a strap, one such approach is recommended for use with the OXIMAX™ and/or MAX-FAST™ sensors developed by Covidien Corporation. While these types of sensors generally provide more accurate readings of a SpO2 than a finger based SpO2 sensor, they are undesirable due to their obtrusive application, with adhesives and straps and the need for reapplication of adhesives when prolonged use (e.g., for more than a few days) is needed.

While various approaches have been proposed for monitoring one or more patient vital signs, such approaches typically require the use of a strap, clamp, glue, headband or the like for a given sensor. It is a given that patients typically do not react positively (i.e., without some modicum of stress) to being "strapped" to sensors or to being attached to fixed diagnostic devices. Accordingly, a long felt and unfulfilled need exists for devices, systems and methods which facilitate the real-time, continuous and unobtrusive monitoring of patient vital signs.

SUMMARY

According to at least one embodiment, a cap device for unobtrusively monitoring a patient's vital signs includes at least one stocking cap, wherein the stocking cap further includes at least one primary compartment configured for receiving a first biometric sensor, at least one third compartment configured for receiving a cartridge, at least one fourth compartment configured for receiving a transmitter, at least one channel configured for routing at least one connector, and at least one fifth compartment configured for receiving an antenna.

According to at least one embodiment, a cap device may also include at least one secondary compartment for receiving a second biometric sensor. Per at least one embodiment, the primary compartment or the secondary compartment may be configured for receiving an SpO2 sensor, such as a MAXFAST sensor. Likewise, at least one of the primary compartment or the secondary compartment of the cap device may be configured for receiving a temperature sensor.

In at least one embodiment, the at least one third compartment of the cap device is configured for receiving at least one of a vital signal pre-processor or a cartridge capable of receiving a SpO2 sensor reading from a patient and determining a pulse oxidation and heart rate for the patient. In at least one embodiment, a fourth compartment of a cap device may be configured for receiving a wireless transmitter. In accordance with at least one embodiment, the third and fourth compartments may be separately or co-located. The cap device may also include at least one channel configured for routing at least one connector between a first biometric sensor situated in one or more primary compartments or one or more secondary compartments and at least one of a vital signal pre-processor and a cartridge situated in another compartment.

According to at least one embodiment, a cap device for use in unobtrusively monitoring a patient's vital signs may include a stocking cap having at least one primary compartment and at least one channel. The cap may also include a first biometric sensor, a first connector, a cartridge, and a transmitter, wherein the first biometric sensor is located within the at least one primary compartment, the first biometric sensor is communicatively coupled to the cartridge via the first connector, and the first connector is routed through the stocking cap using the at least one channel. The cartridge may be communicatively coupled to the transmitter via a second connector. Per at least one embodiment, the first connector may extend outside of the stocking cap, and one or more of the cartridge and the transmitter may be located external to the stocking cap. Per at least one embodiment, the stocking cap may include a third compartment. The cartridge may be located within the third compartment. Per at least one such embodiment, the transmitter may be located external to the stocking cap, and the cartridge is communicatively coupled to the transmitter via a first communications link extending from the third compartment to the transmitter.

According to at least one embodiment, a system for unobtrusively monitoring a patient's vital signs is provided. Such system may include a first biometric sensor configured to output first vital signals, a cartridge, a first connector communicatively coupling the first biometric sensor with the cartridge, a server, and a stocking cap. Per at least one embodiment, the stocking cap includes a primary compartment configured for receiving the first biometric sensor, and a first channel configured for routing the first connector between the first biometric sensor and the cartridge. Per at least one embodiment, the cartridge is configured to receive the first vital signals from the first biometric sensor, process the received vital signals, and output the processed vital signals for transmission to the server. The server may be configured to receive the processed vital signals, convert the processed vital signals into information signals, and output the information signals to one or more presentation devices.

In accordance with at least one system embodiment, the system may include a second biometric sensor configured to output second vital signals, a second connector communicatively coupling the second biometric sensor to the cartridge, and a stocking cap having at least one secondary compartment configured for receiving the second biometric sensor and a second channel configured for routing the second connector between the second biometric sensor and the cartridge. The stocking cap may include a third compartment configured for receiving the cartridge. Per at least one embodiment, the system may include a transmitter communicatively coupled, via a first communication link, to the cartridge and, via a second communications link, to the server. In accordance with at least one embodiment, the server may be cloud based and the transmitter may be communicatively coupled to the server using the Internet.

Per at least one embodiment, a system may include the use of a stocking cap having at least one fourth compartment configured for receiving a transmitter and at least one fifth compartment configured for receiving an antenna, wherein the antenna is used to wirelessly connect the transmitter to the server using the Internet.

This Summary is provided to introduce a selection of concepts in a simplified form that are further described below in the Detailed Description. This Summary is not intended to identify key features or essential features of the claimed subject matter or to be used to limit the scope of the claimed subject matter. A more extensive presentation of features, details, utilities, and advantages of the various embodiments described herein and of the present invention, as defined in the claims presently or hereafter pending, is provided in the following written description of various embodiments of this disclosure and illustrated in the accompanying drawings.

DESCRIPTION

The various embodiments described herein are directed to cap devices, methods and systems which facilitate unobtrusive monitoring of a patient's vital signs. In at least one embodiment, such devices, systems and methods are configured for use in a hospital, urgent care facility, outpatient facility, nursing home, rehabilitation center, home health care or other environment in which real-time monitoring of a patient's vital signs is desired. As used herein for at least one embodiment of the present disclosure, cap devices, systems and methods are described which facilitate unobtrusive monitoring of a patient's vital signs by using one or more biometric sensors which are concealed from the immediate view and access by the patient when such sensor(s) are applied to the patient and while such sensor(s) are monitoring the patient's desired vitals. Further and with respect to at least one embodiment, unobtrusive monitoring of a patient's vitals is facilitated by one or more cap devices containing one or more biometric sensors(s) which do not require the use of glues, straps or similar fastening and/or harness type devices or mechanisms to position and keep the sensor(s) in a desired orientation and/or position with respect to at least one location on a patient's body.

In at least one embodiment, unobtrusive monitoring is facilitated by providing cap devices which facilitate such monitoring while the patient is resting and while the patient engages in a range of permitted activities. In accordance with at least one embodiment, such range of permitted activities are specified by a nurse and may include light physical activities, such as using a restroom facility, eating, watching television, and walking a hall. In accordance with at least one embodiment, unobtrusive monitoring is facilitated by the use of a cap device, as described above and as further described below, in conjunction with one or more systems which enable nurses to continuously receive, track and view, as so desired, a patient's vitals locally and/or remotely. In accordance with at least one embodiment, such unobtrusive monitoring may arise with respect to one or more vital signs and may arise with respect to the remote monitoring of one or more of a patient's vitals by the use of one or more wired and/or wireless and communications and networking systems and technologies which interconnect a cap device to a system configured to facilitate local and/or remote monitoring by nurses using mobile devices, terminals and other user presentation devices.

Figure 1A:
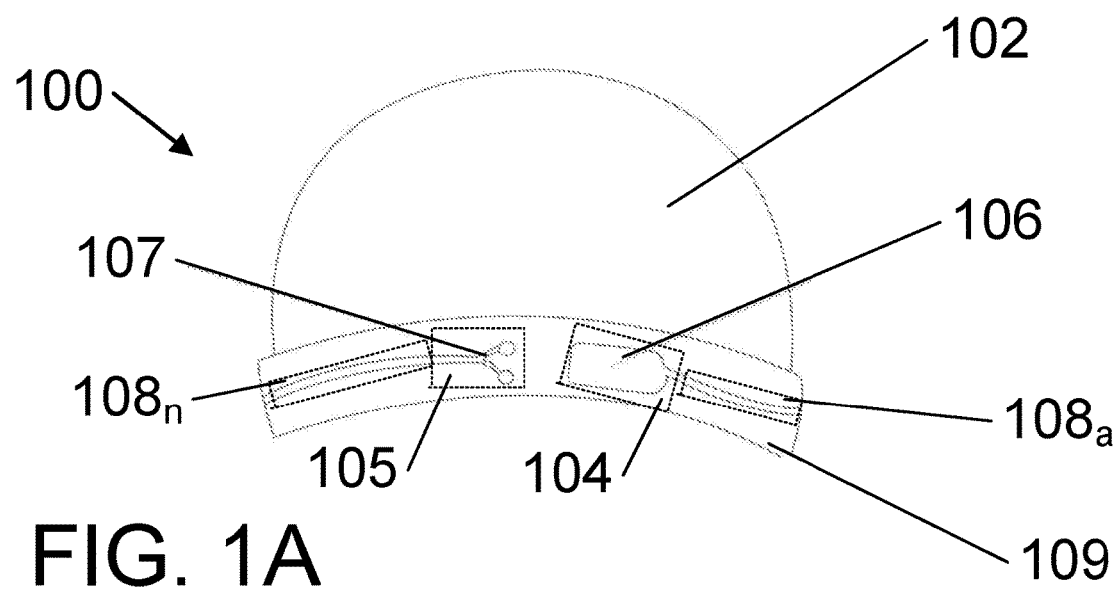
FIG. 1A depicts a front view of a cap device for unobtrusively monitoring a patient's vital signs according to at least one embodiment of the present disclosure.
Figure 1B:
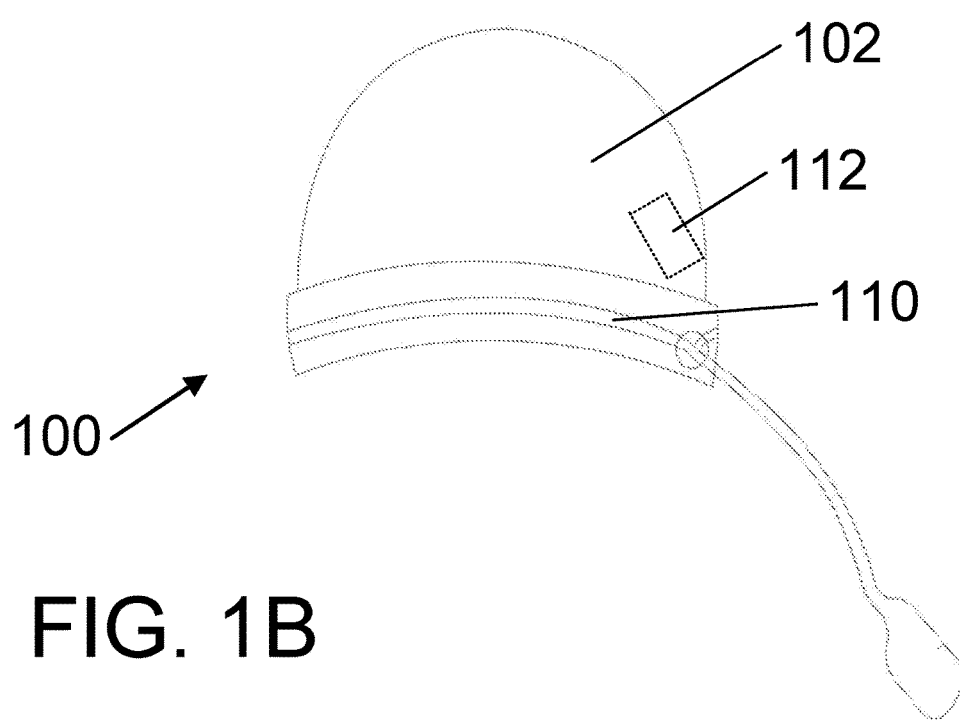
FIG. 1B depicts a side view of the cap device of FIG. 1 for unobtrusively monitoring a patient's vital signs according to at least one embodiment of the present disclosure.

As depicted in FIGS. 1A-1B, one embodiment of a cap device 100 for unobtrusively monitoring a patient's vital signs is configured in the shape of a stocking cap 102, where the stocking cap is configured as a knit cap, a beanie, a HEAD-SWEAT™ or similarly configured to be situated on a patient's head and in close proximity to the contours of a patient's head. It is to be appreciated that stocking cap 102 may be configured of any desired materials including, but not limited to, wool, cotton, synthetic materials, blended materials, or otherwise. Stocking cap 102 may be configured to provide any desired degree of solar and thermal insulation ranging from cool/cold weather insulation, as may be provided by a wool cap to keep a person's head warm during winter type conditions, to cooling insulation effects, as may be provided by a stocking cap 102 configured to wick moisture and heat away from a patient's head, adding a body's natural cooling systems. Stocking cap 102 may be configured in various sizes, shapes and configurations including, but not limited to, as a Scandinavian Tomte, a bobble hat, a Toptue, a Balaclava, and otherwise. Stocking cap 102 may be configured to include one or more extensions, such as the "ears" on a MICKEY MOUSE™ type hat, an aviator hat (having extensions over one's ears), a Capuchon, a Shpitzel, a jester hat, or otherwise. These extensions may include one or more compartments for holding sensors, diagnostic devices, transmitters, or otherwise. Stocking cap 102 may be configured in various sizes ranging, for example, from sizes intended to fit a neo-natal infant to sizes intended to fit grown adults. Other size may also be utilized as desired for any given implementation of one or more of the described embodiments.

As shown in FIGS. 1A and 1B, cap device 100 may be configured to include one or more primary compartments 104 into which a first biometric sensor 106a may be inserted. In accordance with at least one embodiment, each of such one or more primary compartments are desirably positioned on cap device 100 so as to align a given biometric sensor with a location on a patient's head suited for measuring the one or more vital signs the biometric sensor is designed to measure. For example, in at least one embodiment, cap device 100 is configured to include a primary compartment 104a situated on the front portion of cap device 100 so as to align a biometric SpO2 sensor with a patient's superficial temporal artery. Biometric sensors for use in measuring a patient's SpO2 at a forehead position are well known in the art and include the above mentioned OMNI-MAX™\ and MAX-FAST™ sensors and others. The principles of operation of such sensors is beyond the scope of the present disclosure, as is the selection of any particular biometric sensor for a given patient monitoring condition. The one or more primary compartments 104 may be configured to have one or more openings (not shown) via which a given biometric sensor can directly and/or indirectly sense a patient's vital signs. For certain sensors, where close skin proximity is not needed, the opening may be smaller and/or non-existent, as specified by the needs of any given sensor. For other sensors, where optical signals are utilized to monitor a given type of vital sign, the primary compartment 104 to be utilized with such sensor may include opaque or other lens, openings or the like. Likewise, when a certain range or a range of pressures for a given sensor to measure one or more vitals with respect to a given patient is desired, cap device 100 and primary compartment 104 may be configured to present the desired pressure onto the given sensor and thereby onto the patient's body at or proximate to the location of the sensor. It is to be appreciated that the application of such pressures may arise by the use of elastic or other material designed to apply such desired pressures. It is also to be appreciated that the snugness or tightness of the fit of a given cap device 100 may vary with application thereof. A cap device 100 may utilize various mechanisms by which the fit of the cap device 100, as applied to one or more positions on a patient's head, may vary. Such mechanisms may include, but are not limited to, draw strings, elastic materials, expandable air chambers and otherwise.

In accordance with at least one embodiment, cap device 100 may be configured to include one or more secondary compartments 105. These one or more secondary compartments 105 may be configured to position a second sensor 107 at a position on a patient's head best suited, or second best suited when the best position is occupied by a first sensor, for measuring a second of a patient's vital signs. In accordance with at least one embodiment, a temperature sensor may be utilized as the second sensor 107. Cap device 100 may include as many secondary compartments 105 as are desired and/or as needed to monitor vitals of a given patient. Such second sensors 107 may include those use in electroencephalography, measuring temperature, measuring SpO2 or determining other vital signs. Such second sensors 107 and the secondary compartments 105 configured for use therewith, may be positioned on the cap device 100 to correspond to secondary positions on a patient's head. Such secondary compartments 105 may be configured to be of any size and configuration and may be configured to provide a desired secondary pressure by a secondary sensor 107 onto a patient's head. Such secondary pressure may be the same as or different than the pressure provided onto the first sensor 106 by the first compartment 104.

As further shown in FIGS. 1A and 1B, cap device 100 may include one or more channels $108_{a-n}$ for use in routing one or more connectors 110 may be connected to the sensing end of a biometric sensor 106/107. Connectors 110 may be configured to propagate a data signal of any desired characteristic including electrical and optical data signals. In at least one embodiment, at least one of the channel(s) 108 is located within a brim 109 of stocking cap 102. In at least one second embodiment (not shown), the channel(s) may be configured to pass a connector over the top, or over one or more sides of stocking cap 102. It is to be appreciated that the size of the channel and the type of connectors utilized therein may vary based on the types of connections needed for a given biometric sensor. In at least one embodiment, the channels $108_{a-n}$ may be configured to provide padding around one or more connectors. The providing of such padding may increase the relative comfort of the cap device 100 as perceived by a patient/wearer thereof while also hiding the routing of the connector(s) 110 in and through the cap. In accordance with at least one embodiment, the channels $108_{a-n}$ may be positioned and configured for use with permanent and non-removable connectors. Likewise, connectors 110 may be configured, on either end, with connectors that are sensor and/or device specific, universal, or some combination thereof. In at least one embodiment, one or more ends of a connector 110 may be adapted for use with any given type of desired biometric sensor. It is to be appreciated that at least one embodiment described herein facilitates the use of replaceable sensors, where the sensors can be replaced without requiring removal, replacement and/or rerouting of connectors 110. In other embodiments, the channels $108_{a-n}$ may be configured to facilitate insertion, removal, rerouting and/or replacement of connectors 110.

It is also to be appreciated that one or more embodiments facilitate the selection of a stocking cap 102 having aesthetics that appeal to a patient's desires, interests or sense of fashion. As used herein, the "aesthetics" of a stocking cap refer to its colors (of which there may be one or more) and configuration. For example, the aesthetics of cap that appeal to a Denver Broncos fan might include a cap with orange and blue coloring, bearing a Bronco's logo, setting forth prominent player names, numbers, Super Bowl Champion (ships) or similar descriptors, or having a horse head configuration. Similarly, the aesthetics of a cap that might appeal to an Oakland Raiders fan might include a cap having black and silver coloring and/or characteristics commonly associated with the Raiders, such as Norse horns or the like. It is to be appreciated that such team-based aesthetics are commonly accepted and well-known in the marketplace.

Figure 2A:
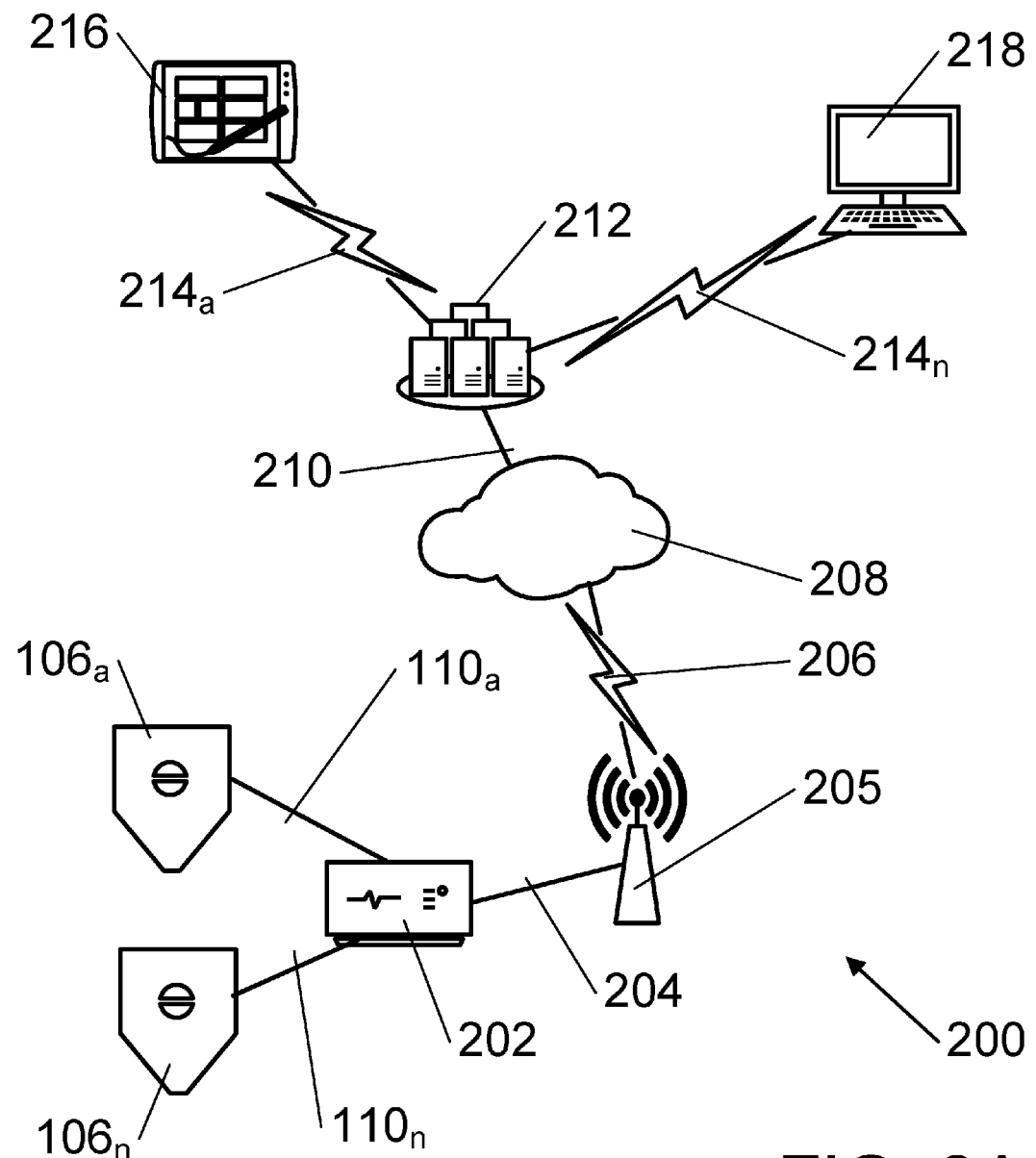
FIG. 2A is a schematic representation of a first embodiment of a system for use with a cap device which facilitates unobtrusive monitoring of a patient's vital signs.
Figure 2B:
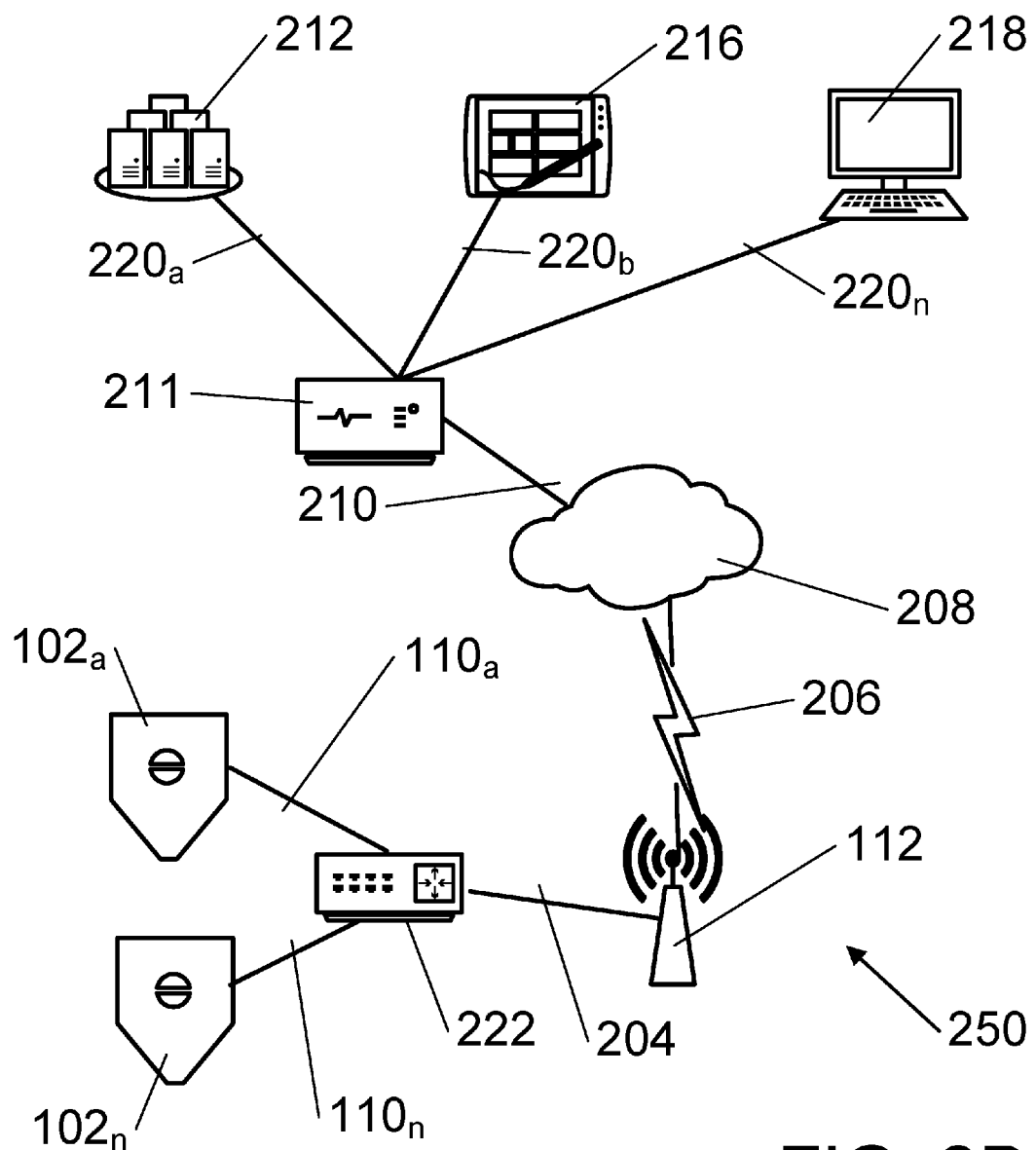
FIG. 2B is a schematic representation of second embodiment of a system for unobtrusively monitoring a patient's vital signs.

As shown in FIG. 1B and as further shown with respect to a first system 200 shown in FIG. 2A and a second system 250 shown in FIG. 2B, cap device 100 may include a third compartment 112 for receiving a cartridge 202 and a fourth compartment (not shown) for receiving a transmitter 205 (FIGS. 2A and 2B). The cartridge 202 and the transmitter 205 being communicatively connected, via one or more connectors 110, to each of the one or more sensors 106 and 107. Transmitter 205 may be directly or indirectly connected to the one or more sensors 106 and 107. In at least one embodiment, sensors 106 and 107 may be connected to a cartridge 202 (FIG. 2A) configured to process the signals provided by the sensor(s) into a desired signal state prior to communication of the sensor readings to other systems and devices by a transmitter 205. Cartridge 202 may be co-located in third compartment 112 with the transmitter 205. An electrical or optical signal may be communicated using a first communications link 204 connecting transmitter 205 to cartridge 202. In at least one embodiment, cartridge 202 may be configured to provide signal processing and diagnostic capabilities comparable to those provided by Philips Corporation's INTELLIVUE MMS X2 ™ device. In at least one embodiment, cartridge 202 may be configured as a portable diagnostic device. Cartridge 202 may be configured to provide lesser or greater signal processing capabilities and/or in other form factors and sizes, as may be desired for any given embodiment of the present disclosure. In accordance with at least one embodiment, cap device 100 may be configured with one or more third compartments 112 for holding such one or more cartridges 202. When configured for storage on the cap device 100 itself, such cartridges 202 are desirably of less than 450 grams. It is to be appreciated that cartridges of such weight are considered herein to facilitate unobtrusive use of the cap device 100 and the monitoring thereby of a patient's vital signs.

As shown in FIG. 2B and in accordance with at least one embodiment, instead of using a cartridge 202 having the more advanced signal processing capabilities of the above mentioned Philips device and similar type devices, a vital signal pre-processor 222 may be utilized to provide a minimal level of vital signal pre-processing such that the vitals are suitable for communication by the transmitter 205 to a remotely located server 212 (FIG. 2A) or a remote diagnostics device 211. Stocking cap 102 may be configured to hold such pre-processor in the third or fourth compartments, as desired for a given embodiment. Examples of such signal pre-processing techniques including noise filtering, signal to noise adjustments, signal amplification, signal band-pass filtering, encryption, compression and other signal processing techniques, any of which may be utilized alone or in combination and as desired for any given embodiment of the present disclosure.

As shown in FIGS. 2A-2B, the transmitter 205 may be communicatively coupled to the cartridge 202 and/or vital signal pre-processor 222. The transmitter 205 may also be communicatively coupled via a second communications link 206 to at least one network 208. Network 208 may be of any desired, known or later arising topology, such as local area networks, cellular networks, wide-area networks, the Internet and others. Network 208 may use any known or later arising wired and wireless communications and networking technologies. Transmitter 205 may be configured to utilize any known or later arising wireless communication technologies that are compatible with the technologies supported by network 208. Such technologies include but are not limited to WIFI, BLUETOOTH, cellular technologies, and others. The network technologies used by network 208 may be configured to support secure communications between the transmitter and one or more distant presentation devices. Such presentation devices may include, but are not limited to, tablet (and other mobile devices) 216, a terminal (and other computer type display devices) 218, a server 212 and other form of devices configured to present biometric sensor data to a nurse in human understandable audible and/or visual forms. Such destination devices being intended for use by a nurse to monitor a patient's vitals real-time, on a delayed, on a historical or another basis. In accordance with at least one embodiment and as shown in FIG. 2A, transmitter 205 may be configured to communicate signals originating from the one or more biometric sensors 106, 107 over secure communications links and networks. Such secure communications links and networks may be established using, for example, virtual private networks, secure socket layers, encryption, two factor authentication, and other known and later arising security technologies. The various types and configurations of secure communications links and technologies that may be utilized in conjunction with the various embodiments described herein are not limited to any particular form or function or principle of operation.

In accordance with at least one embodiment, transmitter 205 may be located at a position in and/or external to the stocking cap 102 so as to emit radiation away from and not into the patient's brain or other body parts. For example, transmitter 205 may be communicatively coupled to one or more antennas (not shown) from which signal 206 is propagated. In one embodiment, the stocking cap 102 may include one or more fifth compartments (not shown) for holding the one or more antennas. In at least one embodiment, the one or more antennas may be located in either or both of the third or fourth compartments. In another embodiment, the antenna, transmitter 205, pre-processor 222 and/or cartridge 202 may be located external to the stocking cap 102 so as to minimize radiation emitted towards a patient. Locations of such components may include, for example, at a patient's hip, at or on a side of a bed, on a stand, or as otherwise positioned for any given implementation. The use of such internal and/or external antenna(s), transmitter 205, pre-processor 222, cartridge 202, connectors 110 providing for communications there between or any combination of the foregoing are considered for purposes of the present disclosure to be consistent with the providing of unobtrusive patient monitoring.

It is to be appreciated that when the transmitter 205 and/or its antenna(s) (not shown) are positioned on the stocking cap 102 itself, various known electromagnetic shielding techniques may be used to minimize and/or reduce the amount of radiation emitted into a patient's brain. For at least one embodiment, such shielding techniques may be integrated into one or more sixth compartments (not shown) in the stocking cap 102. Likewise, for at least one embodiment, an antenna may be situated in one or more distal ends of a given stocking cap 102. For example, stocking cap 102 may be configured in the shape of a Jester's hat, having two or more crown members and into one or more of such crown members an antenna may be situated. The position of an antenna in such one or more crown members may be configured to reduce the amount of radiation emitted by cap device 100 into a patient's brain. It is to be appreciated that other techniques for reducing the amount of radiation emitted into a patient may be utilized for any given embodiment. For example, lower transmission power signal strengths, burst data signaling technologies, electromagnetic frequencies having shorter wavelengths, and other techniques may be utilized to minimize a patient's radiation risk as arising from use of a cap device 100 having electromagnetic signal transmission capabilities.

Referring again to FIGS. 2A and 2B, it is to be appreciated that various communications links and technologies, the nature of which are generally well-known in the art, may be used in accordance with the various embodiments to communicate patient vitals from a transmitting device 205, across network 208, and to one or more presentation devices and/or systems. In addition to those communications links describe above, such communications links include, but are not limited to, a third communications link 210 between the network 208 and a server 212 or a diagnostic device 211, one or more fourth communications links 214a-n between the server 212 and the tablet(s) 216 and terminal(s) 218, and one or more fifth communications links 220a-n between a remote diagnostics device 211 and one or more of the server 212 and the table 216 or terminal 218. Each of such communications links and the devices, network and/or systems connected thereto may utilize any known or later discovered communications technologies including but not limited to Cloud based technologies.

In accordance with at least one embodiment, devices for receiving a patient's vitals, as captured and communicated using a cap device 100, may take various forms. In one embodiment, such vitals may be communicated to a server 212, such as an application server, executing a set of computer software instructions configured to receive the vitals, associate the vitals with a given patient, as established in one or more databases, such as an electronic medical records (EMR) database, and configure such vitals and patient information into a human perceptible form, as presented to a nurse using an audio and visual presentation device, such as a tablet computer, a smartphone, laptop, computer display or other well-known audio and/or visual data presentation devices. It is to be appreciated that the presentation of patient vitals on a smartphone, tablet, laptop, desktop or other form of presentation device may utilize one or more application programs, real-time and/or streaming programs, SMS (short message service, aka texting) based programs or otherwise. In accordance with at least one embodiment, the communication of a patient's vitals for presentation to a nurse may arise based upon one or more patient parameters, such as age, weight, height, sex, medications, medical history, prescribed treatments and any other information deemed relevant by a nurse, or other professional or medical system, with respect to the given patient, a normal patient, as determined for example using a normal distribution, or otherwise. Such parameters may be obtained from and/or associated with the patient's EMR or otherwise obtained from a database communicatively coupled to the server 212. Further, the server 212 may be configured to permit a nurse using a display device, such as table 216 or terminal 218 having an interactive user interface configured, for example, to set alarm parameters, monitoring ranges or other monitoring parameters, such as a patient event, a clinical event, the administration of medications, and the providing of treatments, for a given or even a grouping of patients. The server 212 may be Cloud, local, distributed, single, clustered, blade, virtual, dedicated, non-dedicated or otherwise based and configured as desired for any given embodiment.

As shown in FIG. 2B for at least one embodiment, a second system 250 for using the cap device 100 to provide unobtrusive monitoring of a patient's vitals may not require the use of a server 212 and instead is configured to permit a diagnostic device 211 to communicate patient vitals directly and/or indirectly, e.g., by one or more communications networks, to a suitable presentation device, such as tablet 216 and terminal 218. As shown for the embodiment depicted in FIG. 2B, such diagnostic device 211 may be communicatively coupled to pre-processing device 222 via a transmitter 205 and a network 208. It is to be appreciated, however, that one or more of the network 208 and the transmitter 205 may not be needed in a given embodiment, for example, when the pre-processor 222 is hard-wire communicatively coupled to the diagnostic device 211. Further, it is to be appreciated that diagnostic device 211 may also be communicatively coupled to the server 212 and to a database.

Figure 3:
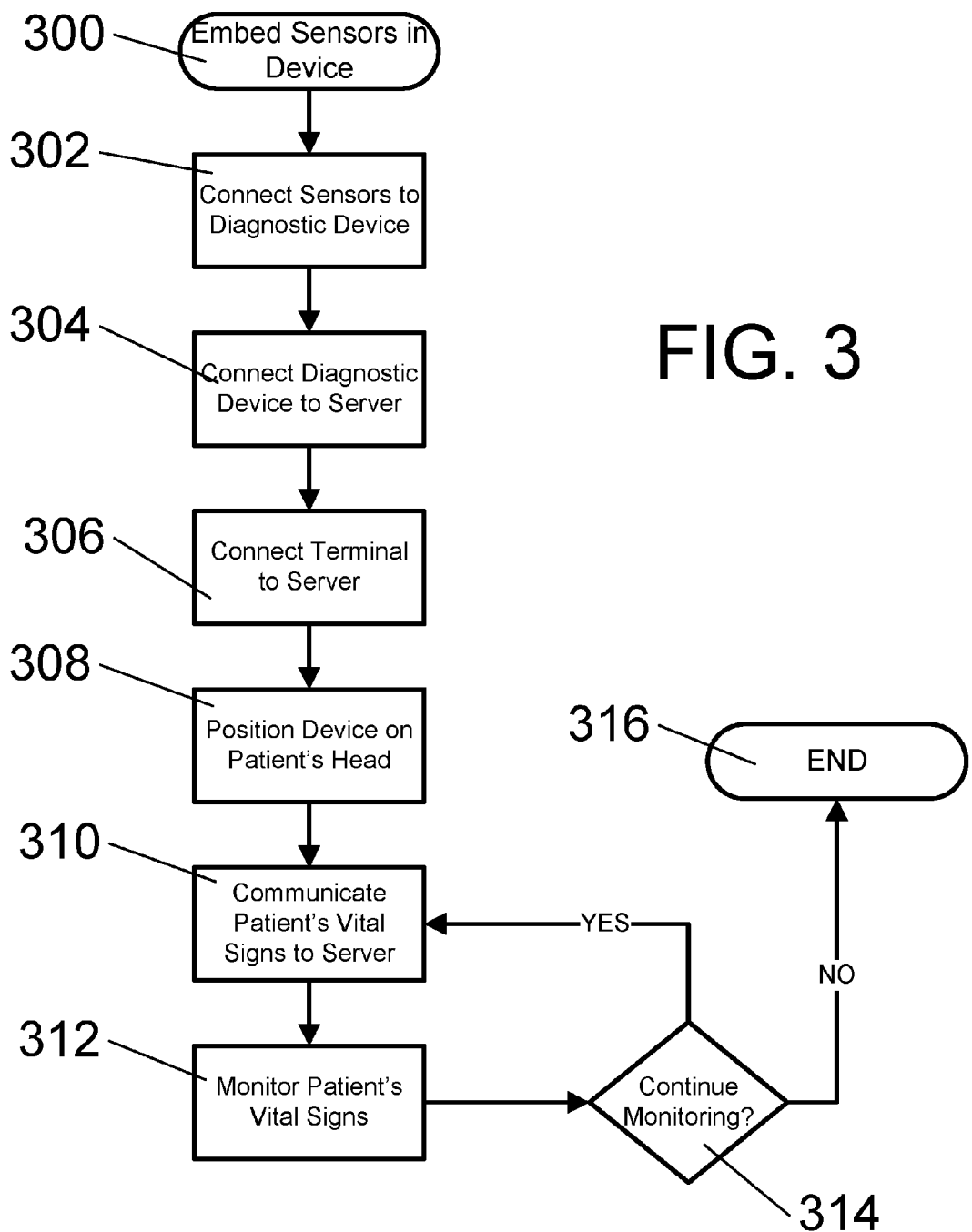
FIG. 3 is a flow chart illustrating one embodiment of a method for unobtrusively monitoring a patient's vital signs using an embodiment of a cap device as described in the present disclosure.

Referring now to FIG. 3, one embodiment of a method for using a cap device 100 to unobtrusively monitor a patient's vitals is described. As shown by Operation 300, this embodiment generally begins when a nurse embeds one or more sensors into a cap device 100. It is to be appreciated that a determination of which sensors to apply to a given patient and the selection of a given cap device 100 for use therewith may vary based on the aesthetics, fit and other preferences, needs and/or characteristics of a given patient. It is also to be appreciated that the type of sensors and the cap device 100 configured for use therewith may vary based on patient needs, patient treatment regimen progressions and regressions, and other parameters. Further, per Operation 300, the activity of embedding sensors in a device may occur prior to a monitoring regimen being prescribed for a given patient. That is, in accordance with at least one embodiment, cap devices 100 may be provided pre-configured for monitoring of one or more certain biometrics, such as SpO2. Likewise, the Operation of embedding sensors in a device may, in accordance with at least one embodiment, include the operation of connecting a given sensor to pre-existing leads located in a compartment configures for use with such sensor. Such an embodiment may be desirable when the cost of the sensor indicates that the sensor is not disposable and may be used to monitor biometrics of two or more patients, with appropriate sterilization of such sensor occurring between such uses. Likewise, it is to be appreciated that for at least one embodiment, the stocking cap 102 may be disposable or intended for a patient to keep, as such patient later desires. Accordingly, Operation 300 for at least one embodiment is intended by this disclosure to be flexible and include other operations, such as inserting one or more leads, cartridges, transmitters and/or antennas into a cap 102, which are needed to configure a cap device 100 for use in one or more of the embodiments described herein to unobtrusively monitor patient vitals, with such configuring of cap device 100 occurring, for at least one embodiment, outside of the range of perception (audible and visual) of a given patient.

Per Operation 302 and for at least one embodiment, the as configured cap device 100 is communicatively connected to a diagnostic device 202. For at least one embodiment, such as the embodiment of FIG. 2A, the communicative coupling may occur using wires directly connecting one or more biometric sensors to a cartridge, with the cartridge itself being a diagnostic device. In other embodiments, the cartridge may provide only some or limited diagnostic capabilities and, in turn, is wirelessly connected to a diagnostic device. Accordingly, it is to be appreciated that the operation of connecting the sensors, as embedded into a stocking cap 102 to a diagnostic device will vary based upon the particular implementation utilized. Likewise, for other embodiments, such as the embodiment shown in FIG. 2B, the operation of connecting the sensor(s) to one or more diagnostic devices may not utilize cartridges and instead may occur indirectly through the use of pre-processors and other signal processing devices, systems and technologies.

Per Operation 304, the diagnostic devices are connected to one or more servers. As discussed above for at least one embodiment, such server is an application server that is communicatively coupled to a database containing a given patient's EMR. It is to be appreciated that the connection of the diagnostic device to the server may include the operation (not shown) of associating a patient's EMR with the data to be received from the one or more biometric sensors. Such step, however, is optional and in certain situations, such as those involving emergency medical treatments in a hospital, ambulance, or even street-side (as provided perhaps by paramedics), may be not needed or desired or consistent with standard of care directives.

Per Operation 306, one or more user tablets, terminals or similar devices are communicatively coupled to the server. It is to be appreciated that this operation may occur in bulk, such as when a nursing station is configured to use one or more presentation devices to present biometric data obtained from multiple patients. Such a situation may arise, for example, in an emergency, intensive care or other nursing station implementations. Per at least one embodiment, in view of patient privacy concerns, the connection of terminals, tablets and other devices to application servers to receive patient specific biometrics may occur only after appropriate user identifications and authentications are provided to the server.

Per Operation 308, a cap device 100 configured with the desired biometric sensor(s) is positioned on a patient's head. For at least one embodiment, the positioning of the cap device 100 occurs without the patient becoming aware of any sensors, leads, cartridges, pre-processors, transmitters or antennas that are or may be embedded into the stocking cap 102. It is to be appreciated, that the positioning of the stocking cap 102 configured as per one or more of the described embodiments may involve the precise positioning and orientation of the cap 102 on the patient's head.

Per Operation 310, the patient's vitals are communicated to the server. As discussed above for at least one embodiment, such vitals are real-time communicated via one or more of the described system embodiments to nurse's presentation device. As used herein, "real-time" means that from the time of sensing of the patient's vital, such as a temperature, to the time of presentation of such temperature on a nurse's presentation device any time delay arising there between is attributable to those data processing, transmission and presentation delays a person of ordinary skill in the art would expect. It is to be appreciated that such delays may total a matter of micro-seconds, or even less, or may be several seconds when, for example, satellite communication links are utilized. For other embodiments, the vitals communicated to the server need not be presented to a nurse real-time and may instead and/or additionally utilized by the server for trending and/or historical monitoring purposes. Such trend and/or historical data may be utilized to determine efficacies of treatment regimens and otherwise.

Per Operation 312, the monitoring of the patients vital(s) occurs. Such monitoring occurs in accordance with nursing instructions or standards of care.

Per Operation 314, a decision is made as to whether a patient's vital(s) require further monitoring. It is to be appreciated that this decision point may be reached based on nursing instructions, standard of care guidelines, patient prognosis, patient improvement, at the time of shift changes or based on any given parameter. When on-going monitoring is desired, Operations 310-312-314 continue. When monitoring can cease, the method ends. Per at least one embodiment, the ending of the method may involve the removal of one or more sensors, cartridges and other components from the stocking cap 102 and the presentation of the stocking cap 102 to the patient as a memento or other keepsake of their care.

In some implementations, articles of manufacture are provided as computer program products that cause the instantiation of operations on a computer system to implement the invention. One implementation of a computer program product provides a non-transitory computer program storage medium readable by a computer system and encoding a computer program. It should further be understood that the described technology may be employed in special purpose devices independent of a personal computer. The above specification, examples and data provide a complete description of the structure and use of the various embodiments of the invention as defined in the claims.

Although various embodiments of the claimed invention have been described above with a certain degree of particularity, or with reference to one or more individual embodiments, those skilled in the art could make numerous alterations to the disclosed embodiments without departing from the spirit or scope of the claimed invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. A cap device for unobtrusively monitoring a patient's vital signs, comprising:
    a stocking cap, wherein the stocking cap further comprises:
    at least one primary compartment configured for receiving a first biometric sensor;
    at least one third compartment, separate from the at least one primary compartment, configured for receiving a cartridge;
    at least one fourth compartment, separate from each of the at least one primary compartment and the at least one third compartment, configured for receiving a transmitter;
    at least one channel configured for routing at least one connector;
        wherein a first channel of the at least one channel is configured to route a first connector from the at least one primary compartment to the at least one third compartment;
        wherein a second channel of the at least one channel is configured to route a second connector from the at least one third compartment to the at least one fourth compartment; and
    at least one fifth compartment, separate from each of the at least one primary compartment, the at least one third compartment, and the least one fourth compartment, configured for receiving an antenna;
        wherein a third channel of the at least one channel is configured to route a third connector from the at least one fourth compartment to the at least one fifth compartment.

2. The cap device of claim 1, comprising at least one secondary compartment for receiving a second biometric sensor.

3. The cap device of claim 1, wherein the first biometric sensor comprises an SpO2 sensor.

4. The cap device of claim 3, wherein the SpO2 sensor is a MAXFAST sensor.

5. The cap device of claim 1, wherein the first biometric sensor comprises a temperature sensor.

6. The cap device of claim 2, wherein the at least one secondary compartment is configured for receiving a temperature sensor.

7. The cap device of claim 1, wherein the at least one third compartment is configured for receiving a vital signal pre-processor.

8. The cap device of claim 1, wherein the at least one third compartment is configured for receiving a cartridge capable of receiving a SpO2 sensor reading from a patient and determining a pulse oxidation and heart rate for the patient.

9. The cap device of claim 1, wherein the transmitter comprises a wireless transmitter.

10. The cap device of claim 1, wherein the at least one channel is configured for routing at least one connector between a first biometric sensor situated in the primary compartment and at least one of a vital signal pre-processor and a cartridge.

11. The cap device of claim 1, wherein the at least one third compartment is collocated with the at least one fourth compartment.

12. A cap device for use in unobtrusively monitoring a patient's vital signs comprising:
    a stocking cap comprising at least one primary compartment, a third compartment, and at least one channel;
    a first biometric sensor;
    a first connector;
    a cartridge located within a third compartment; and
    a transmitter;
    wherein the third compartment is separate from the at least one primary compartment;
    wherein the first biometric sensor is located within the at least one primary compartment, the first biometric sensor is communicatively coupled to the cartridge via the first connector, and the first connector is routed through the stocking cap using the at least one channel.

13. The cap device of claim 12,
wherein the cartridge is communicatively coupled to the transmitter via a second connector,
wherein the second connector extends outside of the stocking cap, and
wherein the transmitter is located external to the stocking cap.

14. The cap device of claim 12,
wherein
the second connector comprises a first communications link communicatively coupling the cartridge with the transmitter.

15. A system for unobtrusively monitoring a patient's vital signs, comprising:
    a first biometric sensor configured to output first vital signals;
    a cartridge;
    a first connector communicatively coupling the first biometric sensor with the cartridge;
    a server; and
    a stocking cap, further comprising:
        a primary compartment configured for receiving the first biometric sensor;
        a third compartment configured for receiving the cartridge;
            wherein the third compartment is separate from the primary compartment;
        a first channel configured for routing the first connector between the first biometric sensor located within the primary compartment and the cartridge located within the third compartment; and
    wherein the cartridge is configured to
        receive the first vital signals from the first biometric sensor,
        process the received vital signals, and output the processed vital signals for transmission to the server;
wherein the server is configured to
receive the processed vital signals and
convert into information signals and
output the information signals to one or more presentation devices.

16. The system of claim 15, comprising
a second biometric sensor configured to output second vital signals,
a second connector communicatively coupling the second biometric sensor to the cartridge, and
wherein the stocking cap comprises
a secondary compartment configured for receiving the second biometric sensor;
wherein the secondary compartment is separate from each of the primary compartment and the third compartment; and
a second channel configured for routing the second connector between the second biometric sensor located within the secondary compartment and the cartridge located in the third compartment.

17. The system of claim 16, comprising
a transmitter communicatively coupled via a first communication link to the cartridge and via a second communications link to the server.

18. The system of claim 17,
wherein the server is cloud based and the transmitter is communicatively coupled to the server using the Internet.

19. The system of claim 18,
wherein the stocking cap further comprises at least one fourth compartment configured for receiving the transmitter and at least one fifth compartment configured for receiving an antenna;
wherein the at least one fourth compartment and the at least one fifth compartment are separate compartments;
wherein the antenna is used to wirelessly connect the transmitter to the server using the Internet.

* * * * *